United States Patent
Rauchschwalbe et al.

(10) Patent No.: US 6,369,239 B2
(45) Date of Patent: Apr. 9, 2002

(54) PROCESS FOR THE PREPARATION OF DIALKYLTHIOPHENES AND ALKYLENEDIOXYTHIOPHENES

(75) Inventors: Günter Rauchschwalbe, Leverkusen; Friedrich Jonas, Aachen, both of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/813,875

(22) Filed: Mar. 21, 2001

(30) Foreign Application Priority Data

Apr. 4, 2000 (DE) ......................... 100 16 723

(51) Int. Cl.$^7$ ..................... C07D 495/04; C07D 333/32
(52) U.S. Cl. ........................... 549/50; 549/62
(58) Field of Search ..................... 549/50, 62

(56) References Cited

U.S. PATENT DOCUMENTS 2,453,103 A    11/1948    Turnbull ................... 260/329

FOREIGN PATENT DOCUMENTS

WO          95/24373        9/1995

OTHER PUBLICATIONS

J. Amer. Chem. Soc., 67, Dec. 1945, pp. 2217–2218, Edward W. Fager, Some Derivatives of 3,4–Dioxythiophene.

Synthetic Communictions, 26(11), (month unavailable) 1996, pp. 2205–2212, M. Coffey, B.R. McKellar, B.A. Reinhardt, T. Nijakowski and W.A. Feld, A Facil Synthesis of 3,4–Dialkoxythiophenes.

Chem. Ber. 43, (month unavailable) 1910, pp. 901–906, O. Hinsberg, Sythetische Versuche mit Thiodiglykolsaureester.

J. Am. Chem. Soc., 73, (month unavailable) 1951, pp. 2956–2957, C. G. Overberger and Joginder Lal, The Preparation of 3,4–Dimethoxy–2,5–dicarbethoxythiophene, 3,4–Dimethoxythiophene.

J. Parkt. Chem., 338 (month unavailable) 1996, pp. 672–674, Andreas Merz and Christina Rehm, Improved Preparation of 3,4–Dimethoxythiophene.

Adv. Mater., 4, Feb. 1992, pp. 116–118, Gerhard Heywang and Friedrich Jonas, Poly(alkylenedioxythiophene)s–New, Very Stable Conduction Polymers.

Synthetic Metals, 41–43, (month unavailable) 1991, pp. 831–836, R. Jonas and L. Schrader Conductive Modifications of Polymers with Polypyrroles and Polythiophenes.

*Primary Examiner*—Bernard Dentz
(74) *Attorney, Agent, or Firm*—Joseph C. Gil; Richard E. L. Henderson

(57) ABSTRACT

A process for the preparation of dialkoxythiophenes and alkylene-dioxythiophenes in high purity and very good yields by decarboxylation of dialkoxythiophene-dicarboxylic acids or alkylenedioxythiophenedicarboxylic acids, respectively, in solvents that have a higher boiling point than the product and contain no nitrogen bases.

7 Claims, No Drawings

PROCESS FOR THE PREPARATION OF DIALKYLTHIOPHENES AND ALKYLENEDIOXYTHIOPHENES

BACKGROUND OF THE INVENTION

The invention relates to a process for the preparation of dialkoxythiophenes and alkylenedioxythiophenes by decarboxylation of dialkoxythiophenedicarboxylic acids and alkylenedioxythiophenedicarboxylic acids, respectively, in solvents that have a higher boiling point than the product and that contain no nitrogen bases.

U.S. Pat. No. 2,453,103 (DuPont, 1948) describes the thermal decarboxylation of 3,4-dimethoxythiophene-2,5-dicarboxylic acid in quinoline at 180–185° C. with addition of a special Cu powder. However, the presence of amines in the end product, even in traces, must be avoided since they interfere in the following step. The workup is therefore carried out by washing with water and acid. The basic quinoline enters the waste water as a salt, which causes environmental pollution or makes an additional, complex step necessary to recover the basic quinoline from the aqueous phase. Even replacement of the Cu catalyst by Cu/Cr oxide (see E. Fager, *J. Amer. Chem. Soc.*, 67 (1945), 2217–2218) does not give better results (58% yield after decarboxylation in quinoline at 180° C. and aqueous/acidic workup).

The same difficulty applies to the procedure of M. Coffey et al., *Synthetic Communications*, 26 (11), 2205–2212 (1996), method 2, which, above all, reveals that Cu (as copper bronze) must advantageously be used in suitable amounts, namely in 1 part per 4 parts of dicarboxylic acid. The requisite temperature of 180–200° C. requires considerable expenditure of energy and apparatus that are not available everywhere. The yield achieved for 3,4-ethylenedioxythiophene (EDT) is only 54%, which is inadequate for industrial application.

This also applies to an increased extent to the method of U.S. Pat. No. 2,453,103, which requires heating at the melting point of the dicarboxylic acid employed for from 2 to 4 hours. The EDT-dicarboxylic acid melts only at temperatures above 300° C. Considerable formation of tar-like materials occurs, which makes the purification by crystallization described in method 1 very difficult and high in losses. In fact, this method is not even described for 3,4-EDT-dicarboxylic acid in the above-mentioned publication.

3,4-Dimethoxythiophene has also been obtained by decarboxylation of 3,4-dimethoxythiophene-2,5-dicarboxylic acid (in the presence of Cu powder, at 180–190° C.) without a solvent. C. Overberger, *J. Am. Chem. Soc.*, 73 (1951), 2956–2957. The high temperature necessary for carrying out the reaction again stands in the way of industrial application. For application to EDT, the comments made in the previous section apply.

In the absence of diluents and metal catalyst, a yield of only 65% is achieved in the purely thermal decarboxylation of 3,4-dimethoxythio-phenedicarboxylic acid to dimethoxythiophene at 250° C. See A. Merz, Chr. Rehm, *J. prakt. Chem.*, 338 (1996), 672–674, in which a product mixture that is obtained must then be separated in a complex manner, i.e. in a number of steps.

EDT and similar 3,4-dialkoxythiophenes are very valuable materials for the preparation of conductive polymers. See, for example, G. Heywang, F. Jonas, *Adv. Mater.*, 1992, 4, 116; F. Jonas, L. Schrade, *Synthetic Metals*, 41–43 (1991), 831–836.

A direct route to such thiophenes starts with the condensation of thiodiacetic acid esters with, for example, oxalic acid esters via 3,4-dihydroxythiophenedicarboxylic acid esters, which can be alkylated, saponified, and decarboxylated (see Hinsberg, *Chem. Ber.*, 43, (1910), 904; and G. Heywang, F. Jonas, *Advanced Materials*, 4 (1992), 116).

A special form of this decarboxylation reaction has now been found.

SUMMARY OF THE INVENTION

The invention therefore relates to a process for the preparation of 3,4-dialkoxythiophenes of the general formula (I) or 3,4-alkylenedioxythiophenes of the general formula (II)

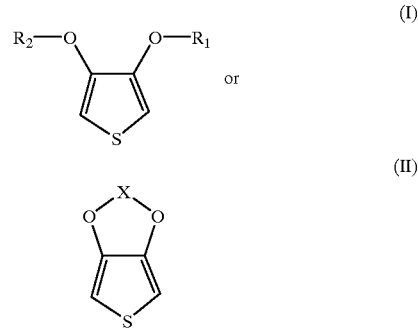

comprising (1) decarboxylating, respectively, a parent 3,4-dialkoxy-2,5-thiophenedicarboxylic acid of the general formula (III)

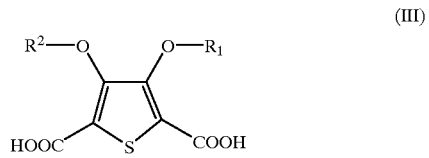

wherein $R^1$ and $R^2$ are straight-chain or branched alkyl having 1 to 15 carbon atoms, or a parent 3,4-alkylenedioxy-2,5-thiophenedicarboxylic acid of the general formula (IV)

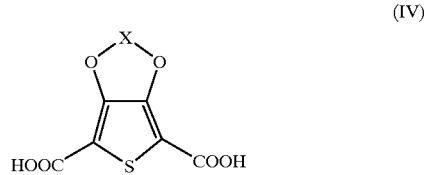

wherein X is optionally substituted —$(CH_2)_n$— and n is an integer from 1 to 12, in a solvent or diluent that has a higher boiling point than the decarboxylated product and is not an aromatic amine, and (2) separating the end product from the higher-boiling solvent or diluent by distillation.

DETAILED DESCRIPTION OF THE INVENTION

The process according to the invention is particularly suitable for the preparation of 3,4-ethylenedioxythiophene (EDT, IUPAC name 2,3-dihydrothieno[3,4-b]-1,4-dioxin):

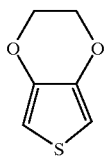

and of the alkyl-substituted compounds derived therefrom, such as a compound of the formula

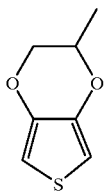

or of 3,4-dimethoxythiophene.

The novel process allows the desired decarboxylation of dialkoxythiophenedicarboxylic acids to give dialkoxythiophenes to be carried out and the resultant products to be worked up in an elegant and simple procedure. The desired products are obtained in very good yield.

The invention is carried out by suspending the starting material, the dialkoxythiophenedicarboxylic acid, in a polar solvent or diluent that has a higher boiling point than the desired dialkoxythiophene. The solvent or diluent preferably has a boiling point which is at least 5° C. higher. If the starting material is employed in aqueous solution or suspension, the water can be distilled off in situ in a first step by heating and distillation. A separate drying step, for example, in a drying cabinet or a paddle dryer, is thus unnecessary.

The decarboxylation is subsequently carried out at elevated temperature, and the product is finally distilled off from the solvent or diluent during or after the decarboxylation. The distillation conditions depend on the physical properties of the product and diluent and on the purity requirements. Thus, for example, a product mixture containing diluent can first be distilled off directly from the reactor and then subjected to rectification. However, the products can also be distilled off in a suitable apparatus, optionally using a column.

In general, a single distillation over a separating column is sufficient to obtain particularly pure products.

The diluent serves, inter alia, for dissipating and distributing the heat supplied via the reactor wall, thus avoiding local overheating.

The decarboxylation reaction can be carried out without a catalyst, i.e. at a temperature of 170 to 260° C. In a preferred embodiment, decarboxylation is carried out in the presence of a catalyst, in which case significantly lower temperatures are sufficient, for example, in the range 100 to 180° C. (preferably at temperatures of from 120 to 170° C., particularly preferably from 130 to 160° C.). The catalyst can be a heavy-metal compound, for example, a copper salt.

The solvents and diluents according to the invention can be, for example, silicone oils, ketones, esters, ethers, sulfoxides, sulfones, or alcohols. However, nitrogen bases, such as quinoline, are unsuitable since, even in traces, they impair the quality of the end products.

Particularly suitable are, for example, Baysilone® (commercial products from Bayer AG), polyethylene glycols, phthalic acid esters, diary ethers, tetramethylene sulfone, diaryl sulfones, and diaryl sulfoxides. Very particularly suitable are Baysilone® and polyethylene glycol 300 and 400, dibutyl phthalate, ditolyl ether, diphenyl sulfone, diphenyl sulfoxide, and tetramethylene sulfone.

For a suitable procedure—depending on the purity of the starting material employed—fresh starting material can be added to the reactor residue, which contains the majority of the diluent, and a new reaction cycle carried out. After a number of cycles, the diluent is then separated off from the dark byproducts, for example, by distillation, by addition of water, or in any other suitable manner, and can be recovered to a considerable extent and reused, which considerably improves the economic efficiency of the process.

In particular, the presence of a diluent simplifies the removal of secondary components, which in turn simplifies cleaning of the reactor after the production campaign.

The catalytically active heavy-metal compound that allows decarboxylation at lower temperature is, for example, basic copper carbonate, copper sulfate, copper oxide, or copper hydroxide.

In a particularly suitable embodiment, moist dialkoxythiophenedicarboxylic acid or alkylenedioxythiophenedicarboxylic acid is introduced into the diluent, heated to above the boiling point of water, and dried by removing water by distillation. If desired, heavy-metal catalyst is then added, the decarboxylation is carried out by heating to the requisite temperature, and the desired product is then removed by distillation (if desired, under reduced pressure). This distillation can initially be carried out without separation, but the distillation can also be carried out using a column at this stage, so that the dialkoxythiophene or alkylenedioxythiophene is obtained in the desired purity. From particularly high-boiling diluents, it is even possible to carry out the distillation at this stage without a separation stage.

Further purification methods for crude distillates that may need to be used if desired are known to the person skilled in the art. Particular mention should be made of washing and chromatography.

The procedure selected depends on external factors, such as, for example, the boiling behavior of the diluent compared with the product, the apparatus available and the cycle times desired.

The outlined variants are intended to describe the invention, but it is in no way limited thereby.

EXAMPLES

Example 1

Uncatalyzed, Purely Thermal Decarboxylation 450 g of dibutyl phthalate were introduced into a stirred flask, after which 240 g of 3,4-ethylenedioxythiophenedicarboxylic acid were added. A vacuum (about 30 mbar) was applied, and the mixture was initially warmed at 150° C. for 1 hour. Water distilled off in the process.

The apparatus was aerated with nitrogen and heated at 240° C. for 24 hours until the evolution of $CO_2$ was complete. The mixture was again cooled, a vacuum was applied, and 3,4-ethylenedioxythiophene was distilled off at 0.1 mbar. 118 g of product (about 80% of theory) were obtained.

Example 2

Catalyzed Decarboxylation 1200 ml of tetramethylene sulfone ("sulfolane") were introduced into a stirred flask, after which 690 g of EDT-dicarboxylic acid (water-moist; the content determination was carried out by liquid chromatography) and 66 g of basic copper carbonate were added. The mixture was heated to an internal temperature of 80° C. at an internal pressure of about 20 mbar, and the water was distilled off. The apparatus was aerated with nitrogen, and the temperature was increased to 140° C. The mixture was stirred at this temperature for 8 hours until the evolution of gas was complete. The mixture was then cooled slightly, a vacuum was again applied (about 20 mbar), and 708 g of EDT/sulfolane mixture was distilled off at an internal temperature of about 150° C.

The same amount of moist EDT-dicarboxylic acid and a little basic copper carbonate were again added to the distillation residue, the amount of sulfolane distilled off was replaced by fresh sulfolane, and the procedure as described was followed.

This replenishment was carried out a total of three times.

In total, 3184 g of EDT/sulfolane mixture that, according to analysis by gas chromatography, comprised 1632 g of pure EDT (95.6% yield) were obtained.

Fine distillation thereof over a short column enabled, after a short preliminary fraction, EDT to be obtained in a yield of 95% (based on the starting materials), a subsequent fraction of sulfolane-contaminated EDT (3%, based on the starting materials; reusable in the next batch) and 1550 g of pure sulfolane, which was likewise reusable.

The identity of the product was confirmed by analysis by gas chromatography (comparison with authentic product).

The residue from the crude distillation was readily pumpable and could be passed to disposal (for example by incineration), but a significant portion of the sulfolane present could also be recovered.

The number of cycles that are possible before disposal depends essentially on the purity of the starting material employed, since impurities accumulate in the distillation still and their amount determines the behavior of the bottom product.

Example 3
Simplified Workup

The procedure was carried out as in Example 2 but after decarboxylation was completed, EDT was distilled off directly via a column. Very pure EDT was obtained in a yield of 95% of theory.

Example 4
Application to 3,4-Dimethoxythiophene 175 ml of sulfolane and 105 g of water-moist, 70% 3,4-dimethoxythiophenedicarboxylic acid (73.5 g (dry)/ 0.316 mol) were introduced into a stirred flask. After 10 g of basic copper carbonate had been added, the mixture was distilled dry at 85° C. and 50 mbar over the course of 1 hour. The apparatus was aerated with nitrogen. At an internal temperature of 140° C., the mixture was stirred until the evolution of $CO_2$ was complete (9 hours). After a further 3 g of copper carbonate had been added, the mixture was stirred for a further 3 hours. 3,4-Dimethoxythiophene was then distilled off using a small column at a bottom temperature of 145° C. and a top temperature of 130° C. 39.5 g of product (0.274 mol/86.7% of theory) were obtained. The identity was confirmed by mass spectrometry and by $^1$H-NMR.

Example 5
Use of Polyethylene Glycol 300 as Solvent 1.5 mol of EDT-dicarboxylic acid were decarboxylated over the course of 20 hours in the presence of 33 g of basic copper carbonate in 600 ml of polyethylene glycol (MW 300) (instead of in sulfolane). EDT was distilled therefrom using a distillation bridge and obtained in a purity of 97.7% and a yield of 96% of theory. Adhering impurities (glycol and diglycol) were removed therefrom by washing with a little water. EDT was obtained in a purity of >99%.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the preparation of 3,4-dialkoxythiophenes of the formula (I) or 3,4-alkylenedioxythiophenes of the formula (II)

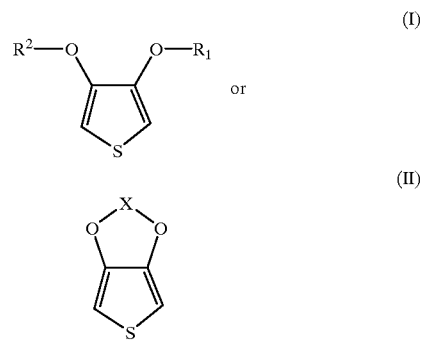

comprising (1) decarboxylating, respectively, a parent 3,4-dialkoxy-2,5-thiophenedicarboxylic acid of the general formula (III)

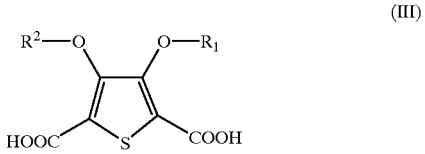

wherein $R^1$ and $R^2$ are straight-chain or branched alkyl having 1 to 15 carbon atoms, or a parent 3,4-alkylenedioxy-2,5-thiophenedicarboxylic acid of the general formula (IV)

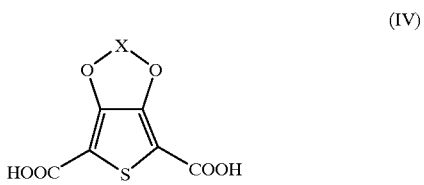

wherein X is optionally substituted —$(CH_2)_n$— and n is an integer from 1 to 12, in a solvent or diluent that has a higher boiling point than the decarboxylated product and is not an aromatic amine, and (2) separating the end product from the higher-boiling solvent or diluent by distillation.

2. A process according to claim 1 wherein the solvent or diluent has a boiling point at least 5° C. higher than the decarboxylated product.

3. A process according to claim 1 wherein the solvent or diluent is a silicone oil, ketone, ester, ether, sulfoxide, sulfone, or alcohol.

4. A process according to claim 1 wherein the decarboxylation is carried out in the presence of a heavy-metal salt.

5. A process according to claim 4 wherein the heavy-metal salt is a copper salt.

6. A process according to claim 1 wherein the decarboxylation is carried out at a temperature in the range from 100 to 180° C.

7. A process according to claim 1 wherein the product is 3,4-dimethoxythiophene or 3,4-ethylenedioxythiophene.

* * * * *